United States Patent [19]

Yabe et al.

[11] Patent Number: 5,449,622
[45] Date of Patent: Sep. 12, 1995

[54] METHOD AND APPARATUS FOR ANALYZING STAINED PARTICLES

[76] Inventors: Ryohei Yabe, 4829-28 Nakane, Katsuta-shi, Ibaraki-ken, Japan; Shinichi Sakuraba, Hans-Sachs-Ring 16, 68199 Mannheim, Germany; Masaaki Kurimura, 560-4, Sugi, Nakamachi, Naka-gun, Ibaraki; Yasuaki Kojima, Tsukubadai-apartment 2-208, 663, Ichige, Katsuta-shi, Ibaraki-ken, both of Japan

[21] Appl. No.: 197,515

[22] Filed: Feb. 16, 1994

[30] Foreign Application Priority Data

Feb. 16, 1993 [JP] Japan ................ 5-026487

[51] Int. Cl.$^6$ .................. G01N 33/48; G01N 33/00; G06F 15/00
[52] U.S. Cl. .................. 436/63; 436/164; 436/171; 436/909; 422/73; 422/82.05; 422/82.09; 250/461.2; 356/38; 356/39; 356/335; 356/407; 356/425; 356/433; 356/436; 356/442; 364/413.08; 364/413.1; 364/413.11; 364/555; 382/6
[58] Field of Search ............ 422/73, 82.05, 82.09; 436/47, 63, 164, 171, 909; 250/461.2; 356/38, 425, 436, 39, 442, 73, 23, 417, 335, 407, 442; 364/413.1, 413.11, 413.08, 555; 382/6

[56] References Cited

U.S. PATENT DOCUMENTS

| | | | |
|---|---|---|---|
| 4,612,614 | 9/1986 | Deindoerfer et al. | 364/415 |
| 4,661,913 | 4/1987 | Wu et al. | 364/500 |
| 4,997,769 | 3/1991 | Lundsgaard | 436/66 |
| 5,116,765 | 5/1992 | Watanabe et al. | 436/165 |
| 5,247,339 | 9/1993 | Ogino | 356/73 |

FOREIGN PATENT DOCUMENTS 3-52573 of 0000 Japan.

*Primary Examiner*—David A. Redding

[57] ABSTRACT

In a stained particle analyzing method and apparatus for staining a test sample containing suspended particles, shooting an image of the stained sample, and classifying the particles and computing the density from the shot image of the sample, the sample, which may not be analyzed precisely, is detected before the start of an image analyzing process. Only the sample, which will be analyzed precisely, is stained and subjected to the image analysis. Color information of the sample before the staining is detected and stored. Color information of an image of the sample shot after the staining is compensated based on the color information of the sample detected before the staining. The sort and density of the particles are classified and computed on the basis of the image after the color compensation.

13 Claims, 11 Drawing Sheets

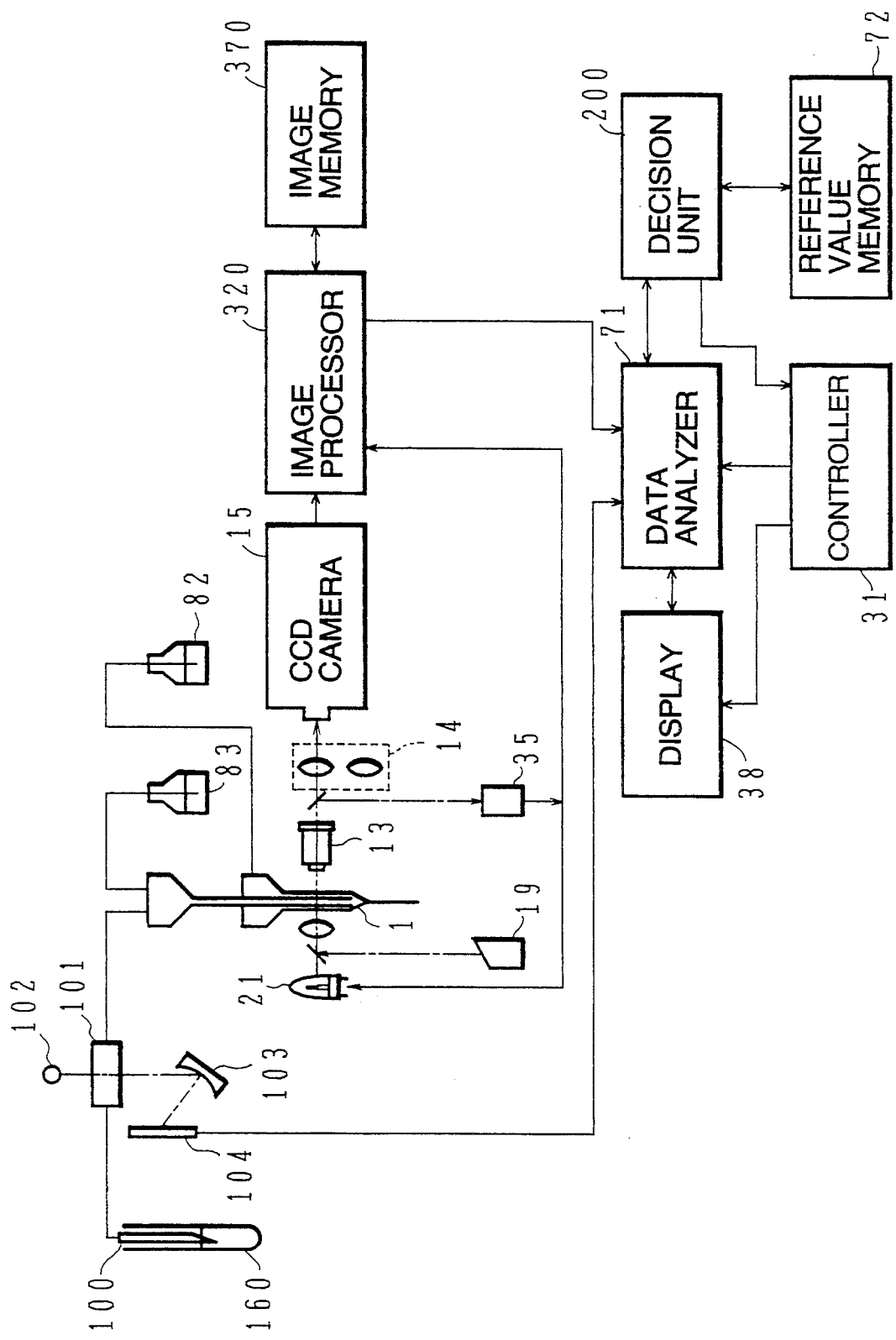

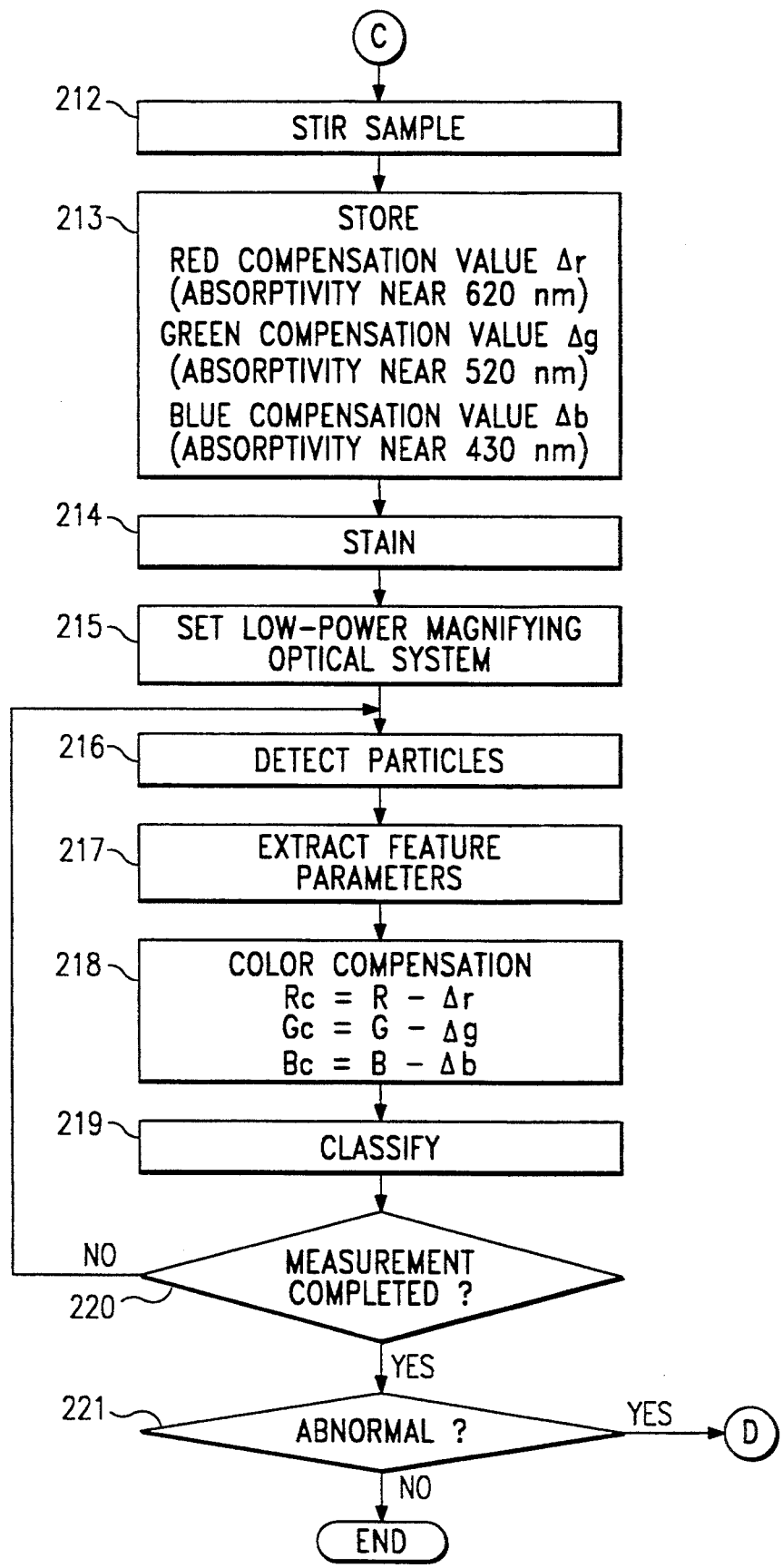

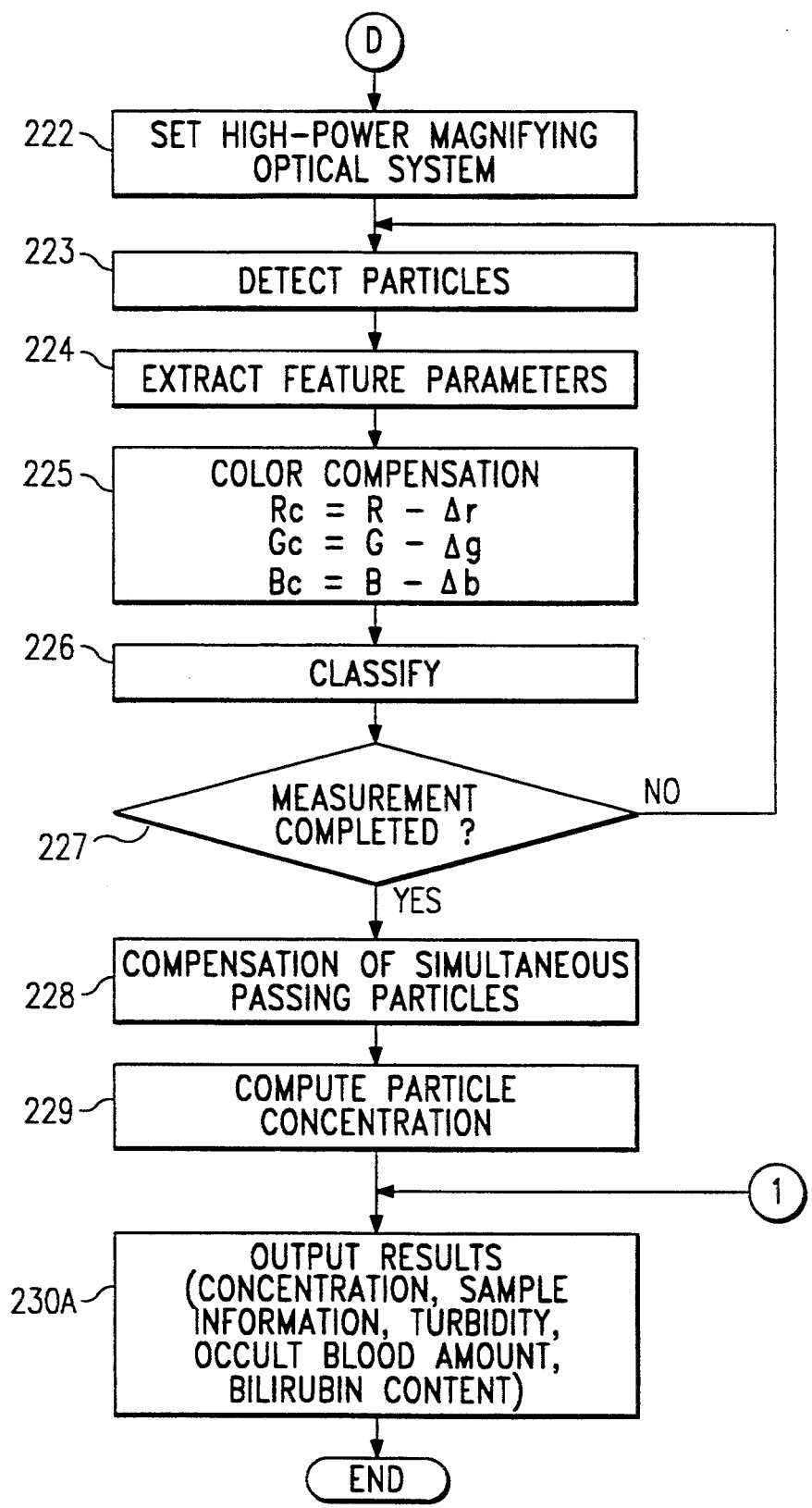

METHOD AND APPARATUS FOR ANALYZING STAINED PARTICLES

BACKGROUND OF THE INVENTION

The present invention relates to a stained particle analyzing method and apparatus which automatically carry out classification of samples from living bodies, such as urine or blood, and concentration measurement and classification of particles contained in those samples.

Hitherto, color measurement of samples from living bodies and measurement of particles contained in the samples have been performed by an exactly manual method which comprises the steps of centrifugally separating a sample from a living body, dipping a deposited sediment onto a slide glass and, if necessary, staining it, preparing a specimen, and visually observing the specimen by an inspection engineer or operator using a microscope.

Apart from such a method of manually measuring particles, "Particle Analyzing Apparatus and Method" has been disclosed in JP, B, 3-52573 as an alternative which can automate measurement of blood cell forms. The disclosed "Particle Analyzing Apparatus and Method" is arranged to flow a liquid containing suspended blood cell particles through a flow cell, optically to shoot an image of the particles, and then to analyze the shot image. Specifically, a sample containing particles is caused to flow through a passage including an image shooting area, a still image of the sample is shot in that area, and the still image is subjected to image analysis.

SUMMARY OF THE INVENTION

When a concentration of particles contained in samples from living bodies is high, e.g., when non-crystalline saline, mucus, red blood corpuscles, white blood corpuscles, etc. are contained in a urine sample at a high concentration, numerous sediment components appear in a resultant still image. With the disclosed prior art, therefore, the image analysis cannot be performed successfully in spite of consuming an extremely prolonged period of time for the analysis, thus leading to a reduction in measurement efficiency.

Also, the disclosed prior art has accompanied a possibility that when stained particles are subjected to the image analysis, particle image information may include an error due to the color of the urine itself before the staining. Therefore, when the disclosed prior art is applied to the image analysis for stained particles, the analysis cannot be made with high accuracy.

It is an object of the present invention to realize a stained particle analyzing method and apparatus which can detect the samples, which may not be analyzed precisely, before the start of image analysis. The stained particles analyzing method and apparatus can stain the samples which will be analyzed precisely, transferring the stained samples to an image analyzing process.

Another object of the present invention is to realize a stained particle analyzing method and apparatus which can detect the samples, which may not be analyzed precisely, before the start of image analysis. The stained particles analyzing method and apparatus can stain the samples which will be analyzed precisely, transferring the stained samples to an image analyzing process, restraining the influence of the color of a urine itself before the staining, analyzing the image with high accuracy.

To achieve the above objects, the stained particle analyzing method and apparatus according to the present invention are constructed as follows.

The stained particle analyzing method according to the present invention comprises the steps of transmitting a light having a plurality of wavelengths through a test sample before staining, and detecting the transmitted light; computing analysis enable/unable decision data, including at least a turbidity of the sample, on the basis of the transmitted light; comparing the analysis enable/unable decision data with a predetermined decision reference value, and determining whether the sample is capable of analysis or not; staining the sample and shooting an image of the sample only when the sample has been determined to be capable of analysis; and classifying particles and computing the concentration on the basis of the image of the sample.

The above stained particle analyzing method, preferably, further comprises the step of displaying the serial number of a sample being incapable of analysis and a notice informing an incapability of the analysis on display means when the sample is determined to be incapable of analysis.

In the above stained particle analyzing method, preferably, the predetermined decision reference value to be compared with the analysis enable/unable decision data is stored in memory means and alterable.

Also preferably, the above stained particle analyzing method further comprises the step of computing color information of the sample on the basis of the transmitted light subsequent to the step of comparing the analysis enable/unable decision data with a predetermined decision reference value. The step of classifying particles and computing the concentration compensates color information of the image of the sample based on the color information computed in the step of computing color information of the sample, classifying particles, computing the concentration of the particles based on the compensated image.

Also preferably, the above stained particle analyzing method further comprises the step of displaying the analysis enable/unable decision data on display means with the classified item and the computed concentration of the particles.

In the above stained particle analyzing method, preferably, the step of computing analysis enable/-unable decision data computes absorptivity of the sample on the basis of the transmitted light, computing the turbidity, the occult blood amount and the bilirubin content of the sample, as the analysis enable/unable decision data, on the basis of the computed absorptivity.

The stained particle analyzing apparatus according to the present invention comprises a light source for emitting a light having a plurality of wavelengths to a test sample; light detecting means for receiving the light passed through the sample, and detecting sample information from the detected light; a flow cell through which the sample is passed; liquid pump means for staining the sample and introducing the sample to pass through the flow cell; image shooting means for shooting an image of the sample in the flow cell; data analyzing means for computing analysis enable/-unable decision data for the sample based on the sample information from the light detecting means, and classifying particles and computing the concentration based on the image of the sample from the image shooting means;

determining means for determining whether the sample is capable of analysis or not on the basis of the analysis enable/unable decision data computed by the data analyzing means; and controlling means for controlling operation of the liquid pump means so that only the sample determined to be capable of analysis by the determining means is stained and passed through the flow cell.

In the above stained particle analyzing method and apparatus, preferably, the analysis enable/unable decision data is data indicating a turbidity, an occult blood amount and a bilirubin content.

Preferably, the above stained particle analyzing apparatus further comprises display means. When the sample has been determined to be incapable of analysis by the determining means, the controlling means controls the display means to display the serial number of the sample being incapable of analysis and a notice informing an incapability of the analysis.

Also preferably, the above stained particle analyzing apparatus further comprises memory means for storing a decision reference value used for determining whether the sample is capable of analysis or not. The determining means compares the decision reference value stored in the memory means with the analysis enable/unable decision data computed by the data analyzing means, and determines whether the sample is capable of analysis or not.

In the above stained particle analyzing apparatus, preferably, the decision reference value stored in the memory means is alterable.

In the above stained particle analyzing apparatus, preferably, the data analyzing means computes color information of the sample based on the sample information from the light detecting means, compensating color information of the image of the sample based on the computed color information, classifying particles, computing the concentration of the particles based on the compensated image.

Preferably, the above stained particle analyzing apparatus further comprises display means. The controlling means controls the display means to display the analysis enable/unable decision data with the classified sort and the computed concentration of the particles.

In the above stained particle analyzing apparatus, preferably, the data analyzing means computes absorptivity of the sample based on the sample information from the light detecting means, computing the turbidity, the occult blood amount and the bilirubin content of said sample, as said analysis enable/unable decision data, on the basis of the computed absorptivity.

BRIEF DESCRIPTION OF THE DRAWINGS

FIG. 5 is a functional block diagram of a control system in a second embodiment of the stained particle analyzing apparatus according to the present invention.

FIGS. 7A, 7B and 7C are flowcharts showing the operation of a second embodiment of the stained particle analyzing method according to the present invention.

DETAILED DESCRIPTION OF THE PREFERRED EMBODIMENTS

Figure 1:
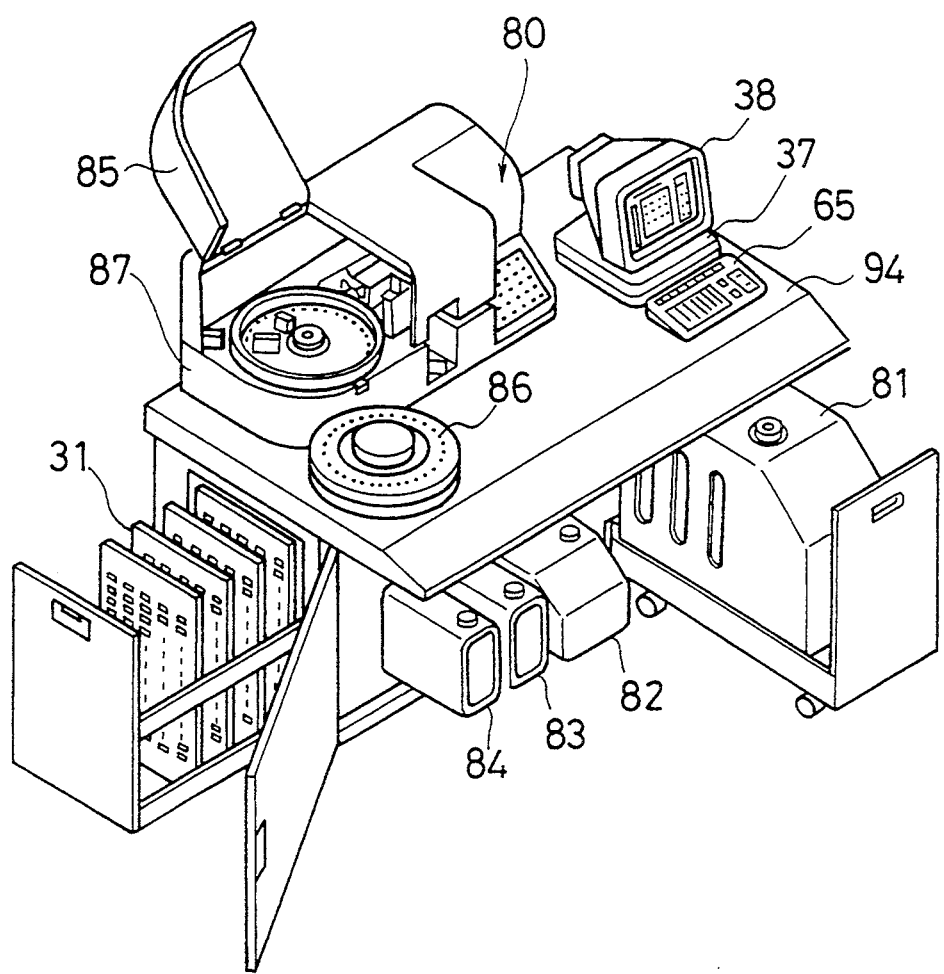
FIG. 1 is an entire schematic perspective view of a first embodiment of a stained particle analyzing apparatus according to the present invention.

FIG. 1 is an entire schematic perspective view of a first embodiment of the present invention, showing the case where the invention is applied to an analyzer for analyzing a sediment in a urine sample.

Referring to FIG. 1, a group of optical measuring devices 80, a CPU 37, a display 38 and a keyboard 65 are arranged on a table 94, whereas a controller 31, a waste tank 81, a rinse bottle 82, a stain solution bottle 83 and a cleanser bottle 84 are arranged under the table 94. The group of optical measuring devices 80 is in continuation to a pre-processing device (or absorptivity measuring unit) 87.

The controller 31 is installed in a rack which is positioned below the table 94 and can be withdrawn to the outside for easier maintenance. The waste tank 81, the rinse bottle 82, the stain solution bottle 83 and the cleanser bottle 84 are arranged such that they can be withdrawn and detached from the front side of the apparatus or the table 94 for easier replacement. The pre-processing device 87 is covered with a cover 85, including a sample disk 86 which can be taken out of the device 87 by opening the cover 85. Over the table 94, there is a space enough for allowing an operator to put the sample disk 86 and carry out sample setting on the table.

The display 38 displays operating conditions of the apparatus and results of the analysis. Therefore, the operator can take necessary steps while confirming the operating conditions of the apparatus and the results of the analysis indicated on the display 38.

Figure 2:
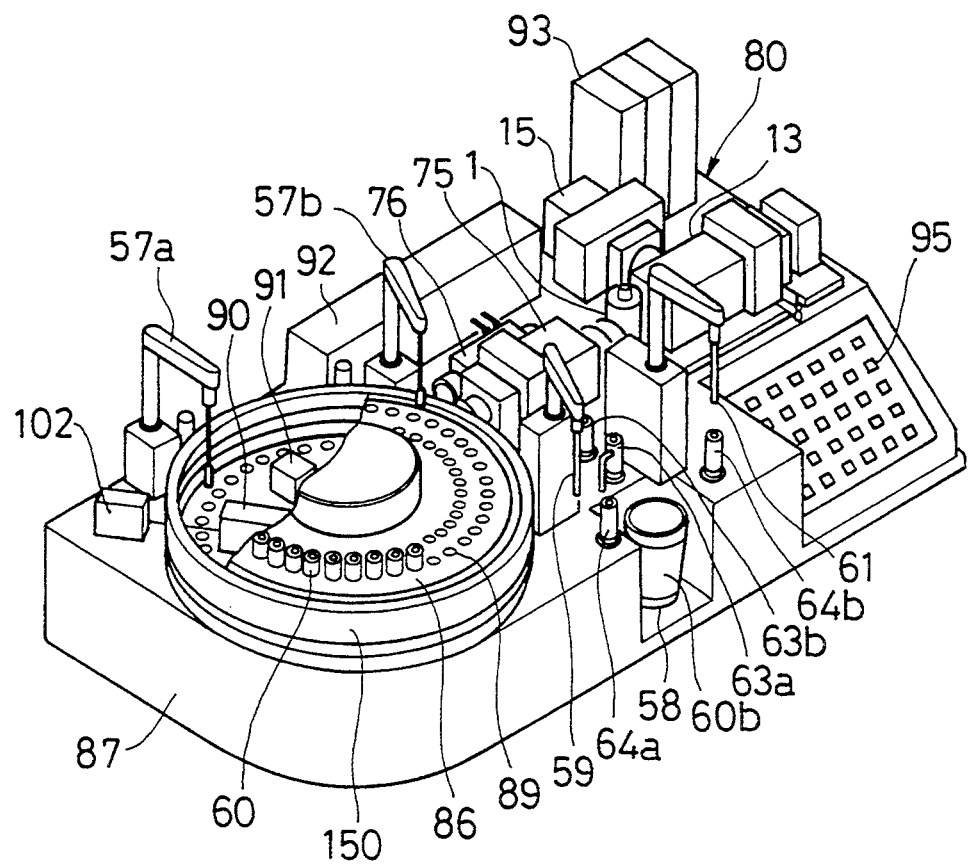
FIG. 2 is a schematic perspective view of a primary part in the first embodiment shown in FIG. 1.

FIG. 2 is a schematic perspective view of the optical measuring device group 80 and the pre-processing device 87 in the apparatus shown in FIG. 1. A turntable 150 is installed on the pre-processing device 87, and the sample disk 86 is detachably disposed on the turntable 150. A number of test tube insertion holes 89 are formed in the sample disk 86. Sample containers 60 are inserted respectively in the test tube insertion holes 89. Under the sample disk 86, there are provided an absorptivity sensor 90 for detecting a plurality of absorption spectra at predetermined monochromatic wavelengths in the visible range of light emitted from a white light source 102, and a bar-code reader 91. A sampling pipette 59, a flow cell pipette 61 and stirrers 57a, 57b are arranged around and near the sample disk 86 in a vertically movable and rotatable manner. Within the radius of a circle along which the sampling pipette 59 rotates, the sample disk 86, a cleansing container 64a and container tanks 63a, 63b are arranged. Within the radius of a circle along which the flow cell pipette 61 rotates, a flow cell 1, a cleansing container 64b and the reaction containers 63a, 63b are arranged. A pulse light irradiator 75 and a solid state irradiator 76 are arranged such that both emitted light rays are irradiated toward the flow cell 1. A microscope 13 is arranged at a position opposite to the pulse light irradiator 75 through the flow cell 1. The flow cell 1, the microscope 13, the pulse light irradiator 75 and the laser beam irradiator 76 are each provided with a mechanism for finely displacing itself so that the mutual positional relationship can properly be adjusted. Further, the optical measuring device group 80 is associated with a solenoid valve 92, a liquid feeder 93 and a control panel 95. Additionally, a CCD camera 15 is arranged in the vicinity of the microscope 13.

Figure 3:
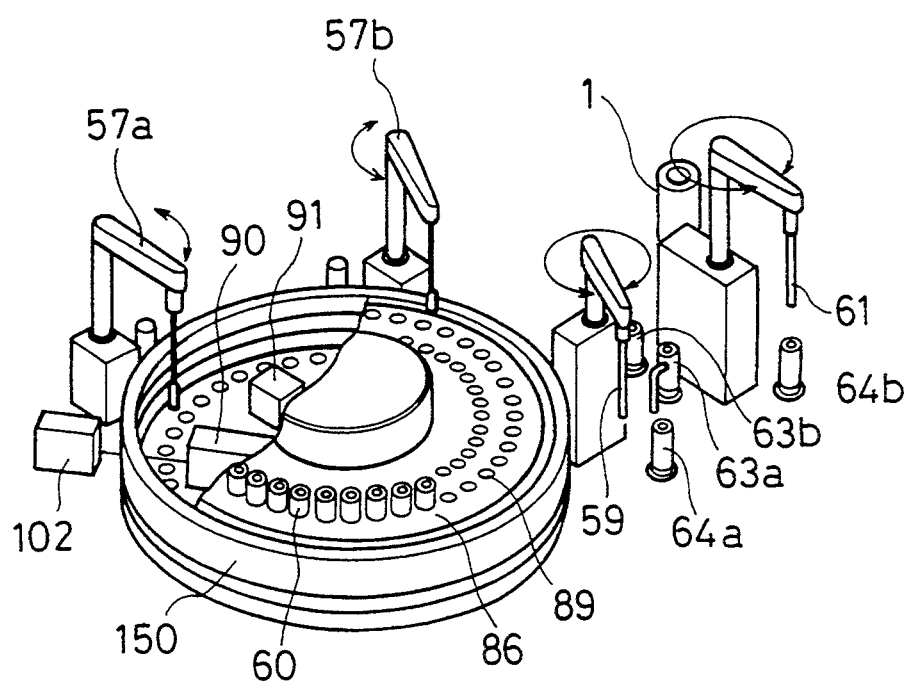
FIG. 3 is a schematic perspective view of a preprocessing device (or absorptivity measuring unit) shown in FIG. 2.
Figure 4:
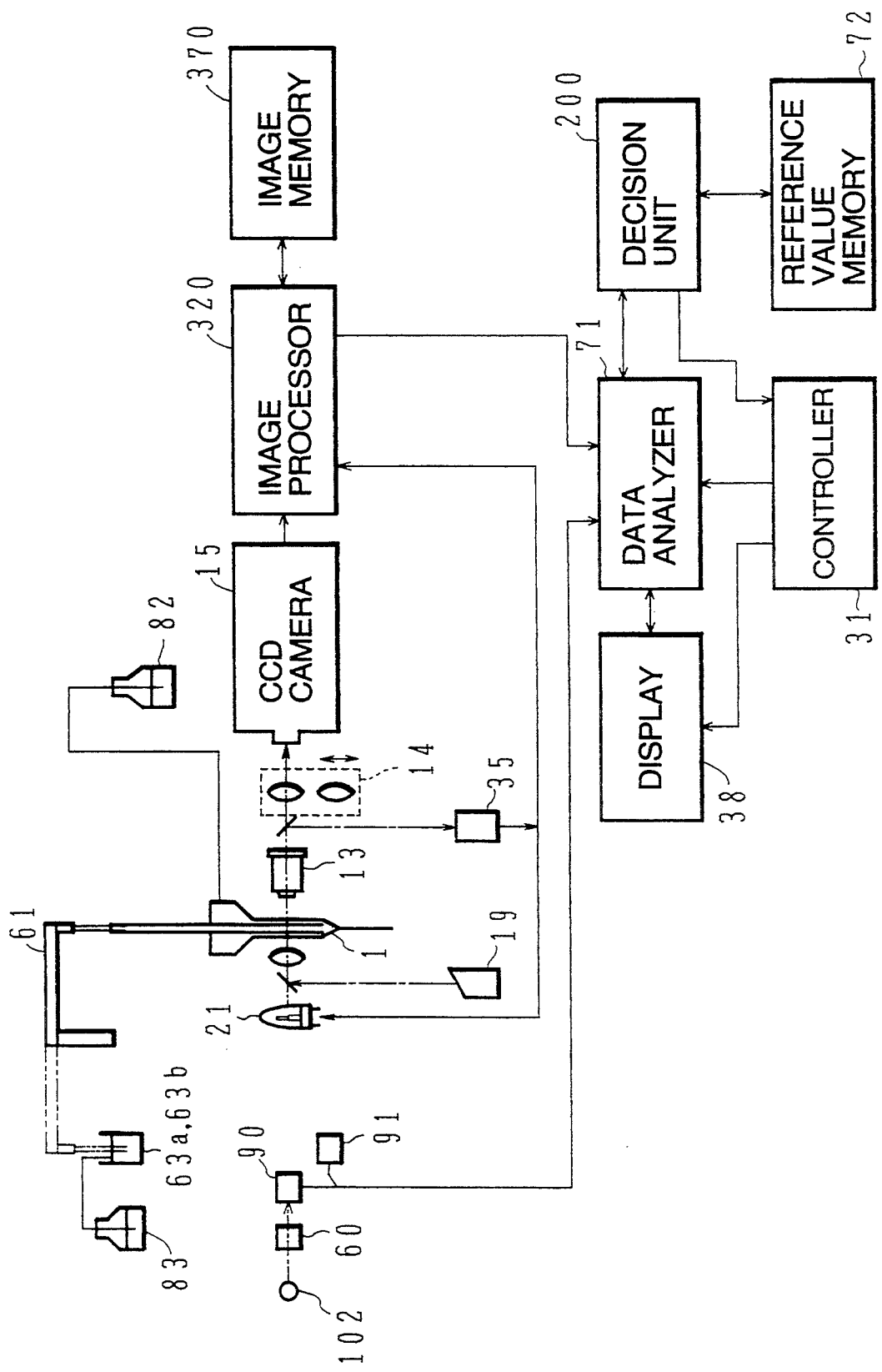
FIG. 4 is a functional block diagram of a control system in the first embodiment shown in FIG. 1.

FIG. 3 is a schematic perspective view of the preprocessing device shown in FIG. 2, and FIG. 4 is a functional block diagram of a control system in the first embodiment shown in FIG. 1.

Referring to FIGS. 3 and 4, the sample containers 60 containing samples are placed in the test tube insertion holes 89 of the sample disk 86, which is then set on the turntable 150. A sheet with a specific bar-code label is stuck to each of the sample containers 60 in advance. By starting the operation of the apparatus after setting the sample disk 86, the turntable 150 is rotated and hence the sample disk 86 is also rotated. During the rotation, the bar-code reader 91 reads the bar code of each sample container 60 for identifying the presence or absence, the item and the serial number of the sample container. Signals indicative of the identified results are supplied from the bar-code reader 91 to a data analyzer 71 for analyzing the signals. The results analyzed by the data analyzer 71 are supplied to a decision unit 200 for determining whether subsequent steps of the measurement are to be continued or not. If any bar code cannot be identified, it is determined that no sample container is present in the test tube insertion hole in problem. The sample in the sample container 60 of which presence has been confirmed by the decision unit 200 is then stirred by the stirrer 57a.

Thereafter, for the stirred sample in the sample container 60, absorptivity of the sample at a plurality of wavelengths are detected by the absorptivity sensor 90 while the sample is kept in a suspended condition, i.e., before sediment components have not been strained. Signals indicative of the detected results are supplied from the absorptivity sensor 90 to the data analyzer 71. Based on the supplied signals, the data analyzer 71 computes contents or amounts of various components or parameters. While the absorptivity is detected by using a white light in this embodiment, monochromatic light rays having different wavelengths may also be used depending on properties of the absorptivity sensor 90 or measurement items of particles to be measured.

The reason that absorptivity at a plurality of wavelengths should be detected for each sample is because various components affecting the measurement exhibit varying absorptivity for different samples. In this embodiment, a component in each sample to be checked is detected by a two-wavelength photometry such that two wavelengths are set as wavelengths adapted for detecting absorptivity of the component or parameter for checking the sample. Then, based on the absorptivity obtained at those two wavelengths, the content of the component contained in the sample and affecting the measurement is detected. Assuming now, for example, that the sample is urine and the parameters to be detected are a turbidity, an occult blood amount and a bilirubin content, an absorptivity in the long wavelength range of the visible wavelength range represents the turbidity, an absorptivity in the medium wavelength range represents the turbidity and the occult blood amount, and an absorptivity in the short wavelength range represents all the three components, i.e., the turbidity, the occult blood amount arid the bilirubin content.

A turbidity X is derived by the data analyzer 71 from the absorptivity difference between suitable two wavelengths (e.g., 660 nm and 700 nm) in the long wavelength range by using the following equation (1):

$$X = \frac{A|660 - 700|}{T|660 - 700|} \quad (1)$$

where $A|660-700|$ is the absorptivity difference of the sample between 660 nm and 700 nm, and $T|660-700|$ is a constant representing the absorptivity difference per unit turbidity.

Then, an occult blood amount Y is derived by the data analyzer 71 from the absorptivity difference between suitable two wavelengths (e.g., 570 nm and 600 nm) in the medium wavelength range by using the following equation (2):

$$Y = \frac{A|570 - 600| - X \cdot T|570 - 600|}{H|570 - 600|} \quad (2)$$

where $A|570-600|$ is the absorptivity difference of the sample between 570 nm and 600 nm, $T|570-600|$ is a constant representing the absorptivity difference per unit turbidity, and $H|570-600|$ is a constant representing the absorptivity difference per unit amount of occult blood.

Further, a bilirubin content Z is derived by the data analyzer 71 from the absorptivity difference between suitable two wavelengths (e.g., 480 nm and 505 nm) in the short wavelength range by using the following equation (3):

$$Z = \frac{A|480 - 505| - X \cdot T|480 - 505| - Y \cdot H|480 - 505|}{B|480 - 505|} \quad (3)$$

where $A|480-505|$ is the absorptivity difference of the sample between 480 nm and 505 nm, $T|480-505|$ is a constant representing the absorptivity difference per unit turbidity, $H|480-505|$ is a constant representing the absorptivity difference per unit amount of occult blood, and $B|480-505|$ is a constant representing the absorptivity difference per unit content of bilirubin.

In the analyzing apparatus shown in FIG. 1, the image analysis is not performed if any value of the above three parameters is too large. The reason is below. For the sample having an excessive value of the turbidity X, numerous sediment components appear in a resultant still image, thus extremely prolonging the time required for the image analysis to a large extent, and the objects to be optically measured are overlapped with each other, thus rendering the region under measurement three-dimensional and making it difficult to effect the precise analysis. For the sample having excessive values of the occult blood amount Y and the bilirubin content Z, the color is so deep that it is very difficult to classify particles and sediments on the still image.

Whether to continuously execute the image analyzing measurement or not is determined by the decision unit 200 based on analysis enable/unable decision data, i.e., the turbidity X, the occult blood amount Y and the bilirubin content Z, computed by the data analyzer 71. Specifically, the decision unit 200 determines whether the computed turbidity X, occult blood amount Y and bilirubin content Z are larger or not than the respective decision reference values which are entered by the operator through the keyboard 65 beforehand and stored in a reference value memory 72, i.e., the reference turbidity Xr, the reference occult blood amount Yr and the reference bilirubin content Zr. Note that the decision reference values stored in the memory 72 are each alterable. The sample which has been determined to be unsuitable for the measurement is judged as one that cannot provide precise measured values with the image analysis. Then, in the apparatus of this embodiment, the serial number of that sample and a notice informing incapability of the analysis are indicated on the display 38. In other words, if the decision unit 200 determines that the sample is unable to analyze, signals representing incapability of the analysis and the serial number of the sample are supplied from the decision unit 200 to the controller 31. In accordance with the supplied signals, the controller 31 controls the display 38 to indicate the serial number of the sample and a notice informing that the sample is unable to analyze, as described above.

For the sample which is capable of continuing the analysis, the data analyzer 71 computes the red compensation value Δr (absorptivity near 620 nm), the green compensation value Δg (absorptivity near 520 nm) and the blue compensation value Δb (absorptivity near 430 nm), these values being stored in a memory within the data analyzer 71.

The sample which has been determined to be suitable for the subsequent measurement by the decision unit 200 is then stirred by the stirrer 57b. Each time the stirrer 57b stirs the sample in one sample container 60, its distal end is brought into a cleansing container 64c to be made clean.

After being stirred, part of the sample is pipetted by the sampling pipette 59. The pipetted sample is selectively supplied to any one of container 63a and 63b, and a stain solution is also supplied by the liquid feeder 93 from the stain solution bottle 83 to the corresponding reaction tank 63a or 63b. The sample and the stain solution are mixed with each other under stirring in the container tank 63a or 63b so that the sample is fully stained. Note that the sample and the stain solution may be supplied in the reversed order of the above steps, or they may be supplied simultaneously. In this embodiment, one sample is stirred in the container 63a, for example, and the next sample is stirred in the container 63b. With such an arrangement, at the time the flow cell pipette 61 has sucked and delivered one sample in the container 63a and has then been cleansed, the next sample is already completely stirred in the container 63b. By so alternately using the containers 63a and 63b, the pipette 61 can suck and deliver a plurality of samples without breaks, enabling the analysis to be executed in a continuous manner.

As an alternative method, the sample may be supplied from a second sample stage 58. In this case, without using the sample disk 86, the sample is put in a sample container 60b which is set on the second sample stage 58. The sampling pipette 59 sucks the sample directly from the sample container 60b and supplies it selectively to the container 63a or 63b.

After stirring a mixture of the sample and the stain solution for a predetermined period of time, the stained sample in the port 63a or 63b is sucked by the flow cell pipette 61. Following the suction, the container 63a or 63b is flushed with a cleanser and the remaining solution is discharged into the waste tank 81.

Subsequently, the flow cell pipette 61 is rotated to a position just above the flow cell 1 and its distal end is inserted to a top portion of the flow cell 1. The distal injecting end of the pipette 61 is designed in size and shape so that it is snugly fitted to an insertion opening of the flow cell 1. Thereafter, the liquid feeder 93 starts supplying a rinse to the flow cell 1 from the rinse bottle 82.

The sample and the rinse are injected by the liquid feeder 93 at a constant speed. After waiting for a sufficient period of time until the flow in the flow cell 1 becomes steady, the stained sample is supplied upon reaching a predetermined flow speed, thereby starting the image analyzing measurement.

A light beam generated by a solid state source 19 enters a particle detector 35 through the flow cell 1 and the microscope 13. The particle detector 35 detects, in accordance with the laser beam incident thereon, that particles will be passing an image shooting area of the flow cell 1. As soon as detecting that particles will be passing the particle detecting area, the particle detector 35 supplies a detection signal to an image processor 320 and a pulse light source 21. The pulse light source 21 generates a pulse light upon receiving the detection signal from the particle detector 35. The pulse light enters the CCD camera 15 through the flow cell 1, the microscope 13 and one of lenses 14 for photographing or shooting the particles in the image shooting area of the flow cell 1.

The image shot by the CCD camera 15 is supplied to the image processor 320 and, after being subjected to image processing, is supplied to an image memory 370. Also, the image processor 320 extracts feature values from the picture supplied thereto and supplies them to the data analyzer 71. The data analyzer 71 subtracts the red compensation value Δr, the green compensation value Δg and the blue compensation value Δb, all previously computed as explained above, from the color information (for red R, green G and blue B) obtained from the image data, thereby carrying out the color compensation. Based on the colorcompensated feature values, the data classifies particles 71 analyzes and computes the concentration of the particles.

Then, the data analyzer 71 indicates the resultant item and concentration of the particles on the display 38.

With the stained particle analyzing apparatus according to the first embodiment of the present invention, as described above, the turbidity X, the occult blood amount Y and the bilirubin content Z are computed based on the measurement of sample absorptivity which is made before the start of image analysis, for determining whether the image analysis is enabled or not. Only the sample which is capable of the image analysis is then transferred to the image analyzing process. As a consequence, it is possible to avoid such an event that the sample can not be analyzed eventually in spite of consuming a lot of time for the image analysis, and hence to improve measurement efficiency.

Further, with the stained particle analyzing apparatus according to the first embodiment of the present invention, color information of a sample is detected before staining the sample, anal feature parameters of particles of the stained sample is compensated with the color information detected before the staining, followed by the image analysis. Accordingly, the influence of urine itself before the staining is so restrained that the image analysis can be performed with high accuracy.

Also, according to the first embodiment of the present invention, when a sample is moved by the flow cell pipette 61 from the pre-processing device 87 to the flow cell 1, the two containers 63a and 63b are alternately used. At the time cleansing the flow cell pipette 61 has come to the end, the sample in either of the reaction tank 63a and 63b is already completely agitated. Consequently, the flow cell pipette 61 can suck and deliver a plurality of samples without breaks, enabling the analysis to be executed in a continuous manner, with the result of still higher measurement efficiency.

In addition, the above-described embodiment may be modified such that the data analyzer 71 first executes coarse classification of samples and then executes fine classification of only the samples which have been determined to be abnormal as a result of the coarse classification.

FIG. 5 is a functional block diagram of a second embodiment of the stained particle analyzing apparatus according to the present invention.

Referring to FIG. 5, a sample container 160 is a urine collecting cup for use in usual urine analysis. A urine sample is contained in the sample container 160.

The sample in the container 160 is sucked by a sampling nozzle 100 and is introduced to a flow cell 101 for measuring an absorptivity. While the sample is passing through the absorptivity measuring flow cell 101, a white light is emitted from a light source 102 to enter the absorptivity measuring flow cell 101. The light transmitted through the flow cell 102 is separated into its spectral components by a light dispersing element 103, and absorptivity of the sample at a plurality of wavelengths are measured by a multi-wavelength detector 104. Based on the measured absorptivity at the plurality of wavelengths, the data analyzer 71 computes the turbidity X, the occult blood amount Y and the bilirubin content Z as sample information, similarly to the above first embodiment. Then, the decision unit 200 compares the computed turbidity X, occult blood amount Y and bilirubin content Z with the respective reference values stored in the memory 72. If the comparison results in that any of the turbidity X, the occult blood amount Y and bilirubin content Z is larger than the reference value, it is determined that the sample in problem is unable to analyze. Thus, the measurement is stopped from transferring to the image analyzing process.

The sample which has been determined to be capable of image analysis is mixed with a stain solution under stirring in the stain solution bottle 83 and is then supplied to the flow cell 1. The subsequent operation is similar to that in the above first embodiment and hence will not be described here.

As described above, the stained particle analyzing apparatus according to the second embodiment of the present invention can provide an advantage below in addition to the similar advantages to those obtainable with the first embodiment.

In the apparatus according to the second embodiment of the present invention, a sample absorptivity is measured by sucking a sample from the sample container 160 and passing it through the absorptivity measuring flow cell 101. Accordingly, the sample container 160 is not required to be of a container having a particular shape. This means that the apparatus can be adapted for urgent analysis which is especially necessitated in the measurement of samples from living bodies, without transferring the sample to a particular sample container. As a result, stained particles can be analyzed more efficiently.

Figure 6A:
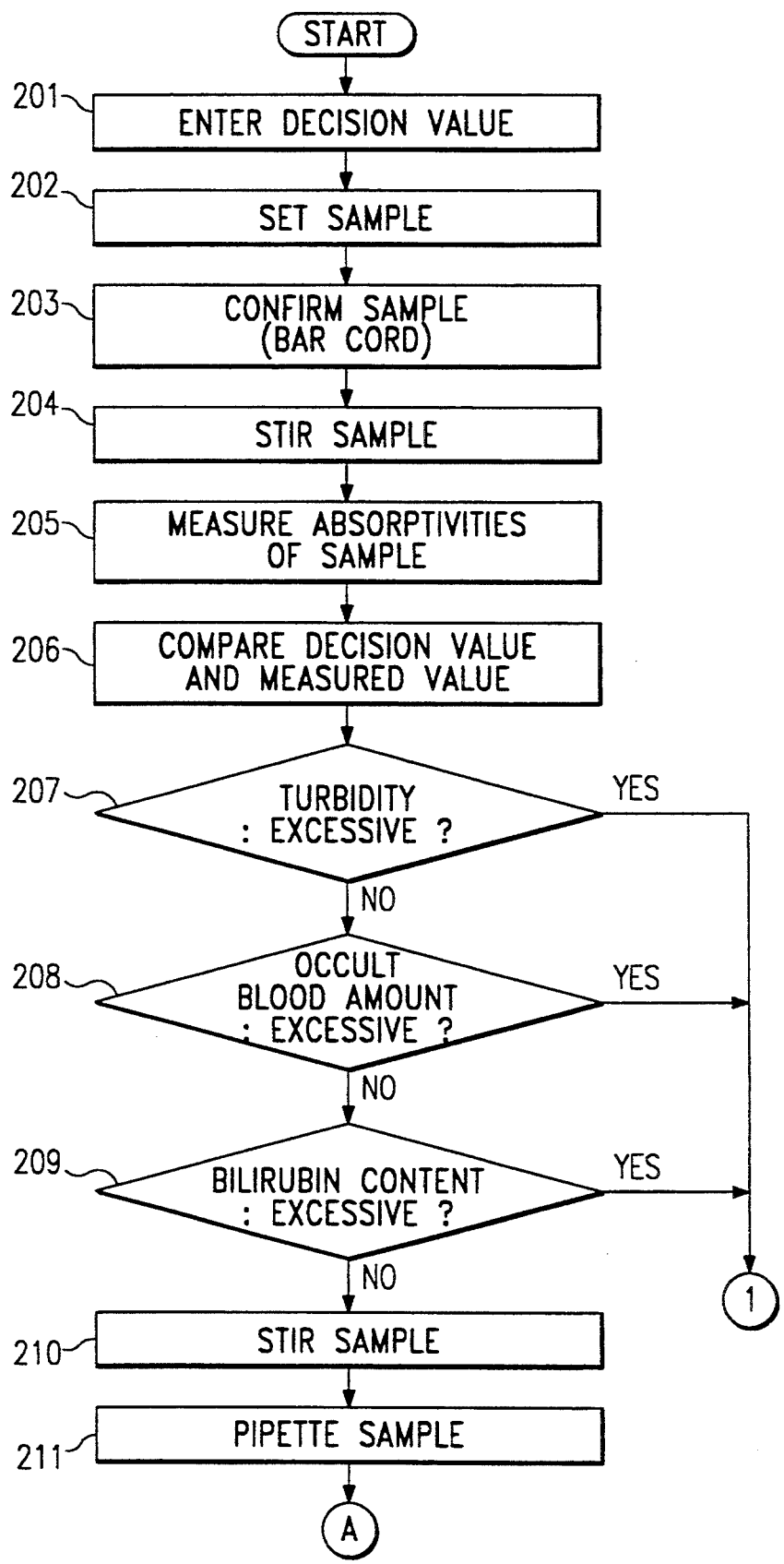
FIGS. 6A, 6B and 6C are flowcharts showing the operation of a first embodiment of a stained particle analyzing method according to the present invention.
Figure 6B:
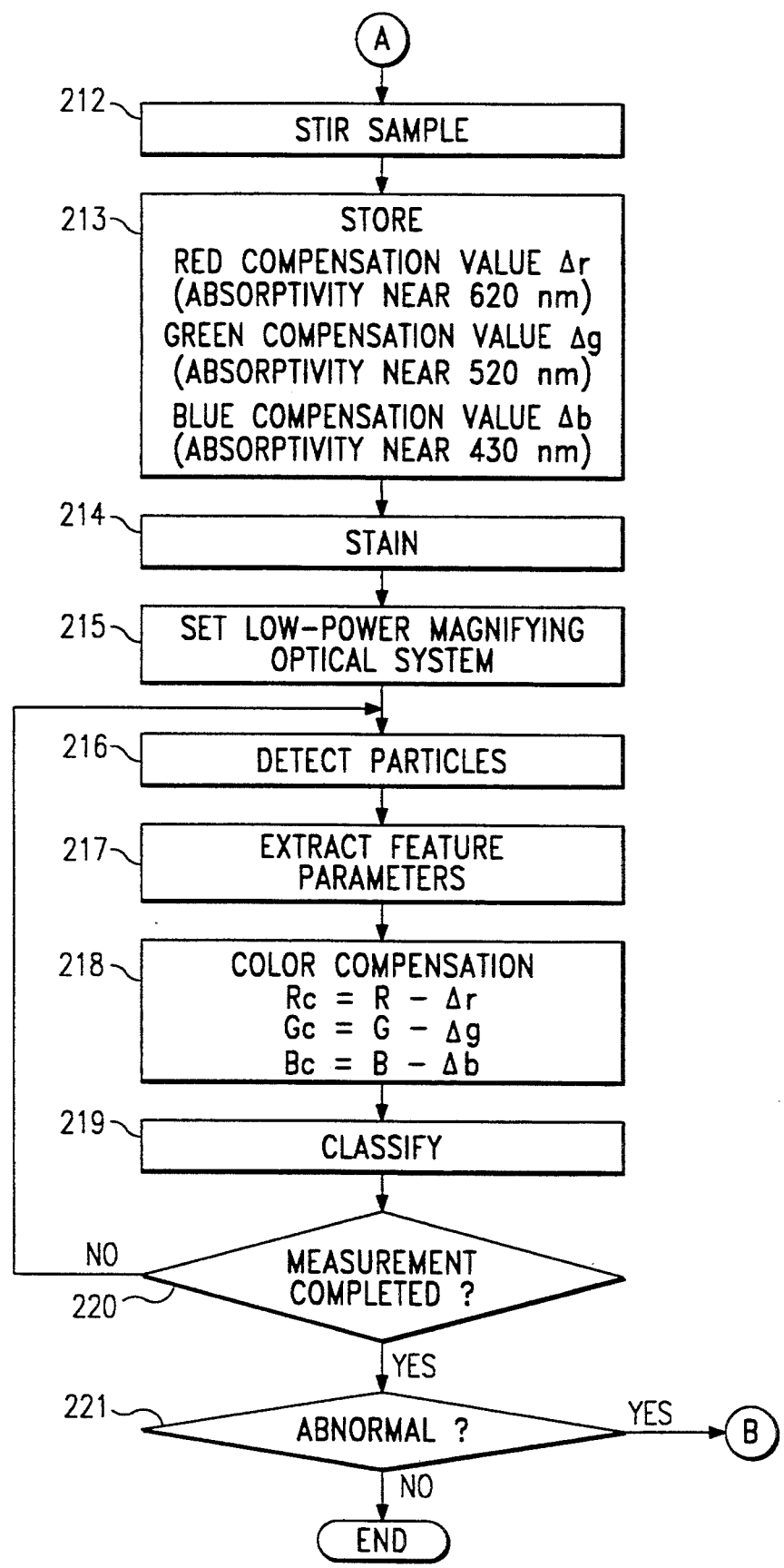
Figure 6C:
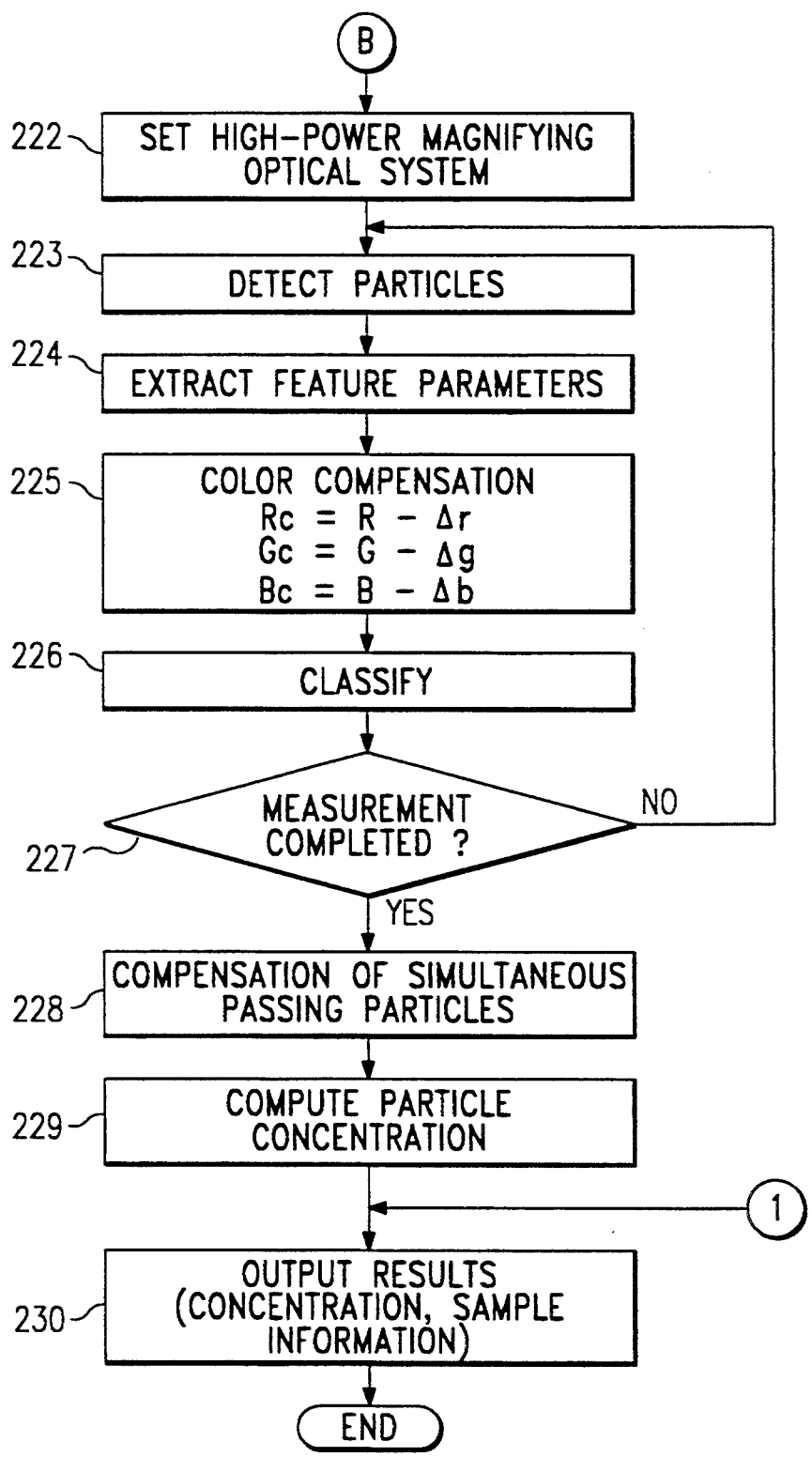

FIGS. 6A, 6B and 6c are flowcharts showing the operation of a first embodiment of a stained particle analyzing method according to the present invention.

In step 201 of FIG. 6A, respective reference values for decision of the turbidity X, the occult blood amount Y and the bilirubin content Z are entered by the operator through the keyboard 65 and are stored in the reference value memory 72. Then, in step 202, test samples are set on the pre-processing device 87. In next step 203, the sort, the serial number, etc. of each of the set samples are read by the bar-code reader or the like. In step 204, the sample is stirred and, in step 205, an absorptivity of the sample is measured.

Subsequently, in step 206, the turbidity, the occult blood amount and the bilirubin content which are computed from the measured absorptivity are compared with the decision reference values stored in the reference value memory 72. Thereafter, if the turbidity X is not larger than the reference value in step 207, then the process goes to step 208. If the occult blood amount Y is not larger than the reference value in step 208, then the process goes to step 209. If the bilirubin content Z is not larger than the reference value in step 209, then the sample is determined to be capable of image analysis and the process goes to step 210.

If any of the turbidity X, the occult blood amount Y and the bilirubin content Z is larger than the corresponding reference value in any of steps 207, 208 and 209, then the process goes to step 230 in FIG. 6C. In step 230, the serial number of the sample in problem and a notice informing that the sample is difficult to analyze are indicated on a CRT or printed out by a printer.

In step 210, the sample being capable of image analysis is stirred and, in step 211 in FIG. 6B, part of the stirred sample is pipetted stirred in step 212. In next step 213, color information of the sample before staining is computed. Specifically, the red compensation value Δr (absorptivity near 620 nm), the green compensation value Δg (absorptivity near 520 nm), and the blue compensation value Δb (absorptivity near 430 nm) are computed and stored.

After that, in step 214, the sample is stained. In step 215, a low-power magnifying optical system is set and, in step 216, particles in the sample are detected. In the embodiment shown in FIG. 4, for example, a low-power magnifying lens of the lenses 14 is brought into the path the light emitted from the pulse light source 21. Then, the sample is introduced to pass through the flow cell 1 and the particles are detected by particle detector and images of particles are shot by the CCD camera 15 or the like.

Next, in step 217, feature parameters are extracted from the detected image or picture of the particles. In step 218, the red compensation value Δr, the green compensation value Δg and the blue compensation value Δb, all previously computed before the staining, are subtracted from color information in the extracted features parameters thereby carrying out color compensation. Further, in step 219, the classification of the particles, etc. are identified based on the image data after being subjected to the color compensation.

The process goes to step 220 for determining whether the measurement of the sample is completed or not. If not completed, then it returns to step 216. If the measurement is completed in step 220, then it goes to step 221 for determining whether the sample is abnormal or not as a result of the analysis using the low-power magnifying optical system. If the sample is abnormal in step 221, then the process goes to step 222 in FIG. 6C. In the step 222, a high-power magnifying optical system is set. In the embodiment shown in FIG. 4, for example, a high-power magnifying lens of the lenses 14 is brought into the path of the light emitted from the pulse light source 21. Then, the sample is introduced to pass through the flow cell 1 and the particles are detected by particle detector and images of particles are shot by the CCD camera 15 or the like in step 223.

Next, in step 224, feature parameters are extracted from the detected image or picture of the particles. In step 225, the red compensation value $\Delta r$, the green compensation value $\Delta g$ and the blue compensation value $\Delta b$, all previously computed before the staining, are subtracted from color information in the extracted feature parameters, thereby carrying out color compensation. Further, in step 226, the classification of the particles, etc. are identified based on the image data after being subjected to the color compensation.

The process goes to step 227 for determining whether the measurement of the sample is completed or not. If not completed, then it returns to step 223. If the measurement is completed in step 227, then it goes to step 228 for carrying out compensation of simultaneous passing particles. In other words, when many particles pass the image sensing area of the flow cell 1, it often occurs that a plurality of particles simultaneously pass the area while image processing. In such a case, despite that a plurality of particles exist in fact, it leads to false counting of particles that only one particle is present. As a result, the computed density of particles becomes incorrect. In view of the above, the number of the particles which pass simultaneously is compensated statistically beforehand and is added to the actual number of the particles for compensation.

Subsequently, in step 229, the concentration of the particles is computed. In step 230, the results such as the computed concentration and the identified item of the particles are output to the CRT or printer, thereby ending the process.

With the stained particle analyzing method according to the first embodiment of the present invention, as described above, whether the sample is capable of image analysis or not is determined before starting the image analysis, and the image analyzing process is executed on only the sample which is capable of image analysis. Consequently, the analyzing method is realized which can avoid such an event that the sample can not be analyzed eventually in spite of consuming a lot of time for the image analysis, and hence can improve measurement efficiency.

Further, with the stained particle analyzing method according to the first embodiment of the present invention, color information of a stained sample is compensated based on color information of the sample obtained before the staining. Consequently, the influence of the color that particles possessed before the staining is so restrained as to realize the analyzing method which can perform the analysis with high accuracy.

Figure 7A:
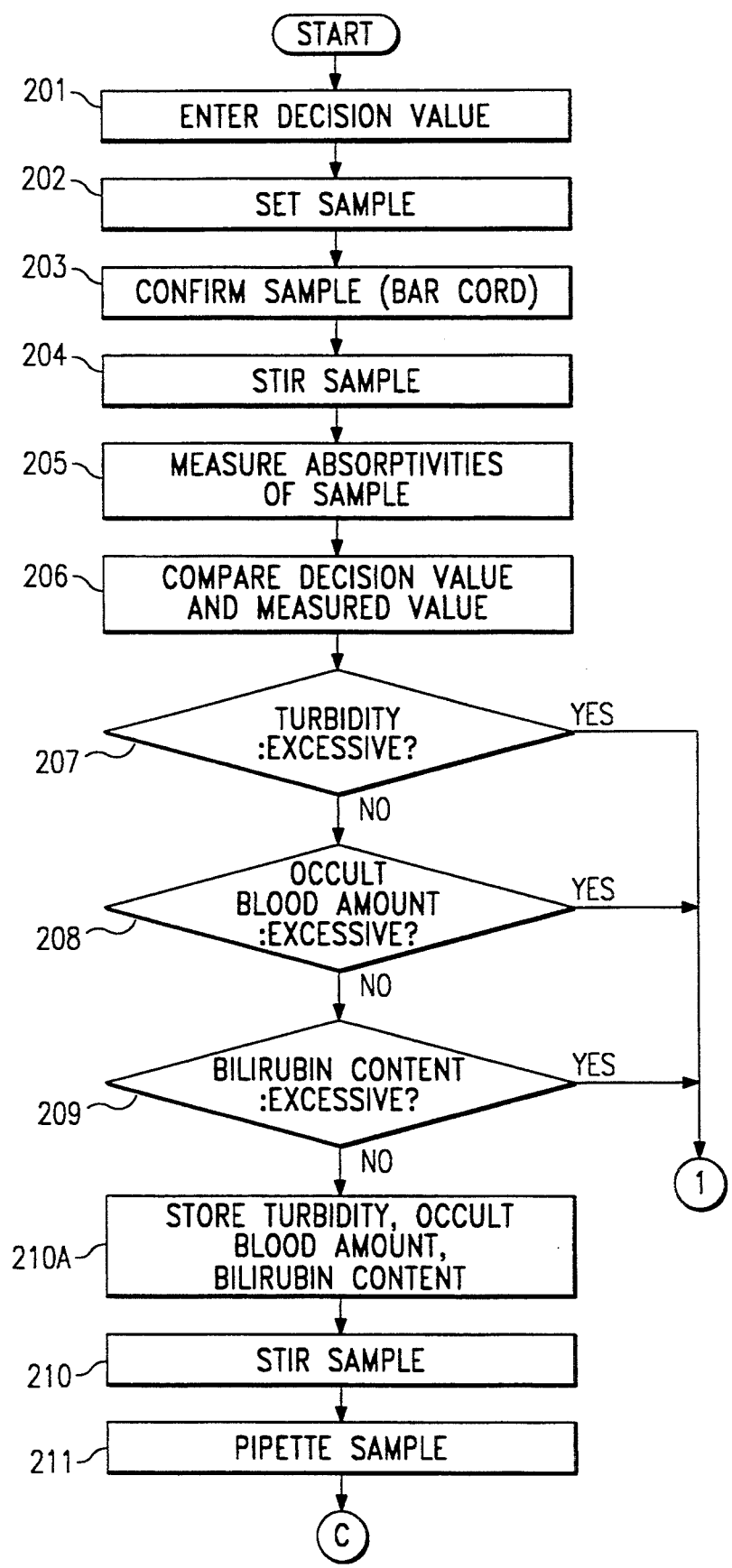

FIGS. 7A, 7B and 7C are flowcharts showing the operation of a second embodiment of the stained particle analyzing method according to the present invention. The second embodiment shown in FIGS. 7A, 7B and 7C is different from the first embodiment shown in FIGS. 6A, 6B and 6C in that the embodiment shown in FIGS. 7A, 7B and 7C includes step 210A between steps 209 and 210, and step 230A in place of step 230 after step 229. The other steps are the same as those in the embodiment shown in FIGS. 6A, 6B and 6C. Therefore, the embodiment shown in FIGS. 7A, 7B and 7C will be described below in relation to only the steps which are not included in the embodiment shown in FIGS. 6A, 6B and 6C.

In step 210A, the turbidity X, the occult blood amount Y and the bilirubin content Z, all computed in step 205, are stored in a memory (not shown). The stored turbidity X, occult blood amount Y and bilirubin content Z are then output in step 230A to the CRT or printer along with the concentration of the sample, the classification of the particles, etc. Indicating the actual values of the turbidity X, the occult blood amount Y and the bilirubin content Z of the sample helps the operator estimate reliability on the concentration of the sample and the classification of the particles resulted from the analysis.

With the stained particle analyzing method according to the second embodiment of the present invention, as described above, it is possible not only to present similar advantages to those obtainable with the first embodiment shown in FIGS. 6A, 6B and 6c, but also to enable the operator to estimate reliability on the analyzed results such as the concentration of the sample and the classification of the particles by indicating the turbidity X, the occult blood amount Y and the bilirubin content Z of the sample, all measured before staining, along with the concentration of the sample and the classification of the particles resulted from the analysis.

What is claimed is:

1. A stained particle analyzing method for staining a test sample of urine taken from a living body and containing suspended particles, shooting an image of said sample after staining, and classifying said particles and computing the concentration of said particles from the shot image of said sample, said method comprising the steps of:

transmitting a light having a plurality of wavelengths through a test sample of urine before staining, and detecting the transmitted light;

computing analysis enable/unable decision data, including at least a turbidity of said sample, on the basis of said transmitted light;

computing first color information of said sample prior to staining on the basis of said transmitted light;

comparing said analysis enable/unable decision data with a predetermined decision reference value, and determining whether said sample is capable of analysis or not;

staining said sample and shooting an image of said sample only when said sample has been determined to be capable of analysis;

computing color compensating information for said image based upon said first color information; and classifying particles and computing the concentration of said particles on the basis of the area, length and the shape of said image of said sample and said color compensating information.

2. A stained particle analyzing method according to claim 1, wherein said analysis enable/unable decision data is data indicating a turbidity, an occult blood amount and a bilirubin content.

3. A stained particle analyzing method according to claim 1, further comprising the step of displaying the serial number of a sample being incapable of analysis and a notice informing an incapability of the analysis on display means when said sample is determined to be incapable of analysis.

4. A stained particle analyzing method according to claim 1, wherein said predetermined decision reference value to be compared with said analysis enable/unable decision data is stored in memory means and alterable.

5. A stained particle analyzing method according to claim 1, further comprising the step of displaying said analysis enable/unable decision data on display means with the classification of the particles and the computed concentration of said particles.

6. A stained particle analyzing method according to claim 1, wherein said step of computing analysis enable/unable decision data computes absorptivity of said sample on the basis of said transmitted light, computing the turbidity, the occult blood amount and the bilirubin content of said sample, as said analysis enable/unable decision data, on the basis of the computed absorptivity.

7. A stained particle analyzing apparatus for staining a test sample of urine taken from a living body and containing suspended particles, classifying said particles in said sample, and computing the concentration of said particles, said apparatus comprising:
a light source for emitting a light having a plurality of wavelengths to said sample;
light detecting means for receiving said light passed through said sample, and detecting said sample information from the detected light;
a flow cell through which said sample is passed;
liquid feeding means for staining said sample and introducing said sample to pass through said flow cell;
image shooting means for shooting an image of said sample in said flow cell;
data analyzing means for computing analysis enable/unable decision data for said sample, for computing first color information of said sample prior to staining based on said sample information from said light detecting means, for computing color compensation information after staining based upon said first color information, and for classifying particles and computing the concentration based on the area, length and the shape of the image of said sample and said color compensation information;
means for determining whether said sample is capable of analysis on the basis of the analysis enable/unable decision data computed by said data analyzing means; and
controlling means for controlling operation of said liquid feeding means so that only test samples of urine determined to be capable of analysis by said means for determining is stained and passed through said flow cell.

8. A stained particle analyzing apparatus according to claim 7, wherein said analysis enable/unable decision data is data indicating a turbidity, an occult blood amount and a bilirubin content.

9. A stained particle analyzing apparatus according to claim 7, further comprising display means, wherein when said sample has been determined to be incapable of analysis by said determining means, said controlling means controls said display means to display the serial number of said sample being incapable of analysis and a notice informing an incapability of the analysis.

10. A stained particle analyzing apparatus according to claim 7, further comprising memory means for storing a decision reference value used for determining whether said sample is capable of analysis or not, wherein said determining means compares the decision reference value stored in said memory means with the analysis enable/unable decision data computed by said data analyzing means, and determines whether said sample is capable of analysis or not.

11. A stained particle analyzing apparatus according to claim 10, wherein said decision reference value stored in said memory means is alterable.

12. A stained particle analyzing apparatus according to claim 7, further comprising display means, wherein said controlling means controls said display means to display said analysis enable/unable decision data along with the classification of the particles and the computed concentration of said particles.

13. A stained particle analyzing apparatus according to claim 7, wherein said data analyzing means computes absorptivity of said sample based on the sample information from said light detecting means, and computes the turbidity, the occult blood amount and the bilirubin content of said sample, as said analysis enable/unable decision data, on the basis of the computed absorptivity.

* * * * *